United States Patent [19]
Crotty et al.

[11] Patent Number: 5,824,326
[45] Date of Patent: Oct. 20, 1998

[54] ACTIVITY ENHANCEMENT OF FERULIC ACID WITH DIMETHYL ISOSORBRIDE IN COSMETIC COMPOSITIONS

[75] Inventors: Brian Andrew Crotty, Branford; Alexander Paul Znaiden, Trumbull; Anthony Johnson, Fairfield, all of Conn.

[73] Assignee: Chesebrough-Pond's USA Co., Division of Conopco, Inc., Greenwich, Conn.

[21] Appl. No.: 884,177

[22] Filed: Jun. 27, 1997

[51] Int. Cl.$^6$ ........................................... A61K 7/48
[52] U.S. Cl. ................................ 424/401; 424/59; 424/62
[58] Field of Search ................................ 424/401, 59, 62

[56] References Cited

U.S. PATENT DOCUMENTS

| | | | |
|---|---|---|---|
| 5,476,661 | 12/1995 | Pillai et al. | 424/401 |
| 5,523,090 | 6/1996 | Znaiden et al. | 424/401 |
| 5,536,499 | 7/1996 | Znaiden et al. | 424/401 |

FOREIGN PATENT DOCUMENTS

| | | |
|---|---|---|
| 55/033451 | 3/1980 | Japan . |
| 59/067213 | 4/1984 | Japan . |
| 52/55037 | 10/1993 | Japan . |
| 53/10526 | 11/1993 | Japan . |

*Primary Examiner*—Venkat Jyothsna
*Attorney, Agent, or Firm*—Milton L. Honig

[57] ABSTRACT

A cosmetic composition is provided which includes ferulic acid or its $C_1$–$C_{30}$ alcohol esters and dimethyl isosorbide in a pharmaceutically acceptable carrier. Dimethyl isosorbide enhances skin lightening, antioxidant and other skin activities of ferulic acid and its esters.

9 Claims, No Drawings

5,824,326

ACTIVITY ENHANCEMENT OF FERULIC ACID WITH DIMETHYL ISOSORBRIDE IN COSMETIC COMPOSITIONS

BACKGROUND OF THE INVENTION

1. Field of the Invention

The invention relates to enhancing the activity of ferulic acid in cosmetic compositions.

2. The Related Art

Ferulic acid and its esters have long been recognized for their skin activity. U.S. Pat. No. 5,476,661, U.S. Pat. No. 5,536,499 and U.S. Pat. No. 5,523,090, all to Pillai et al., report ferulic acid as a skin lightening agent. JP 55/033451 (Morita) reports the oryzanol esters of ferulic acid as being active against dry skin, as well as suppressing dandruff and itchiness. Oryzanol is a triterpene alcohol. Oryzanol ferulate esters have been reported in JP 52/55037 (Eisai) as naturally deepening the black color tone of hair and skin. JP 59/067213 (Suga) describes ferulate esters as having antioxidant properties, especially for alleviating effects of ultraviolet rays on polyunsaturated fatty acids. JP 53/10526 (Eisai) connects both the acid and the oryzanol esters to the prevention of skin aging and wrinkling.

Literature on these actives is voluminous. Only a small sampling of the art has been described above. Yet with all the recognition, ferulic acid and its derivatives have not been significantly exploited commercially. A major reason is that these compounds are quite difficult to deliver into the skin. The present invention addresses this problem.

Accordingly, it is an object of the present invention to provide cosmetic compositions containing ferulic acid or its esters which are formulated in a manner which improves delivery of the actives into human skin.

Another object of the present invention is to provide cosmetic compositions containing ferulic acid or its esters which function to lighten skin and provide an antioxidant effect.

These and other objects of the present invention will become more readily apparent from consideration of the following summary, detailed description and Examples.

SUMMARY OF THE INVENTION

A cosmetic composition is provided that includes:

(i) from 0.01 to 5% by weight of ferulic acid or a $C_1$–$C_{30}$ alcohol ester of ferulic acid;

(ii) from 0.1 to 20% by weight of dimethyl isosorbide; and (iii) a pharmaceutically acceptable carrier.

DETAILED DESCRIPTION OF THE INVENTION

Now its has been discovered that ferulic acid or its $C_1$–$C_{30}$ esters can have their skin lightening, antioxidant and other skin activities enhanced through use of dimethylisosorbide in a pharmaceutically acceptable carrier. Dimethyl isosorbide is known in Chemical Abstracts as 1,4:3,6 dianhydro-2,5-di-o-methyl-D-glucitol. Commercially it is available from ICI Surfactants under the trademark Arlasolve DMI. Amounts of this material may range from 0.1 to 20%, preferably from 0.5 to 10%, optimally from 1 to 8% by weight of the cosmetic composition.

Ferulic acid is available from several sources including Seltzer Chemicals, Inc., Carlsbad, Calif. Esters of ferulic acid are derived from esterification with a $C_1$–$C_{30}$ alcohol. Examples include methyl ferulate, ethyl ferulate, isopropyl ferulate, octyl ferulate and oryzanyl ferulate. Amounts of ferulic acid or its esters may range from 0.01 to 5%, preferably from 0.1 to 3%, optimally from 1 to 2% by weight of the cosmetic composition.

Compositions of this invention usually require a pharmaceutically acceptable carrier. Generally the carrier will be an ingredient present in highest amounts in the cosmetic composition. These amounts may range from 10 to 99.9%, preferably from 25 to 90%, optimally from 50 to 85% by weight of the cosmetic composition. Carriers typically include polyols, silicones, carboxylic esters and combinations thereof.

Polyols are particularly suitable as carriers in the compositions of this invention. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, glycerin, ethoxylated glycerin, propoxylated glycerin and mixtures thereof. Most preferably the polyol is a mixture of polyethylene glycol, molecular weight ranging from 200 to 2,000, and propylene glycol. Preferred weight ratios of polyethylene glycol to propylene glycol range from 5:1 to 1:10, preferably from 2:1 to 1:5, optimally 1:1 to 1:2. Amounts of the polyol may range from 1 to 50%, preferably from 10 to 40%, optimally from 25 to 35% by weight of the cosmetic composition.

Silicone oils may also be included as carriers in the compositions of this invention. These oils may be either volatile or nonvolatile. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms. Cyclomethicone is the common name of the preferred volatile silicone oil and is available as a tetramer or pentamer. Amounts of the volatile siloxane will range from 10 to 80%, preferably from 20 to 70%, optimally from 30 to 65% by weight of the composition.

Linear volatile silicone materials generally have viscosities less than about 5 centistokes at 25° C. while cyclic materials typically have viscosities of less than about 10 centistokes.

Examples of preferred volatile silicone oils useful herein include: DC 344, DC 345, DC 244 and DC 245 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The nonvolatile silicone oils useful in compositions of this invention are exemplified by the polyalkyl siloxanes, polyalklyaryl siloxanes and polyether siloxane copolymers. The essentially nonvolatile polyalkyl siloxanes useful herein include, for example, polydimethylsiloxanes with viscosities of from about 5 to about 100,000 centistokes at 25° C. Among the preferred nonvolatile silicones useful in the present compositions are the polydimethylsiloxanes having viscosities from about 10 to about 400 centistokes at 25° C. Such polyalkyl siloxanes include the Viscasil series (sold by General Electric Company) and the Dow Corning 200 series (sold by Dow Corning Corporation). Polyalkylaryl siloxanes include poly(methylphenyl)siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Cetyl dimethicone copolyol and cetyl dimethicone are especially preferred because these materials also function as emulsifiers and emollients. The former material is available from Goldschmidt AG under the trademark Abil EM-90. Amounts of the nonvolatile siloxane may range from 0.1 to 40%, preferably from 0.5 to 25% by weight of the composition.

Esters may also be incorporated into the cosmetic compositions as pharmaceutically acceptable carriers. Amounts may range from 0.1 to 50% by weight of the composition. Among the esters are:

(1) Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate. Particularly preferred are $C_{12}$–$C_{15}$ alcohol benzoate esters.

(2) Alkenyl esters of fatty acids having 10 to 20 carbon atoms. Examples thereof include oleyl myristate, oleyl stearate, and oleyl oleate.

(3) Ether-esters such as fatty acid esters of ethoxylated fatty alcohols.

(4) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(5) Wax esters such as beeswax, spermaceti, myristyl myristate, stearyl stearate.

(6) Sterols esters, of which cholesterol fatty acid esters are examples thereof.

Aesthetic properties and stabilization of emulsions incorporating ferulic acid or its esters and dimethylisosorbide combination may be improved through addition of a crosslinked non-emulsifying siloxane elastomer, Average number molecular weight of these elastomers should be in excess of 1,000, preferably in excess of 1 million and optimally will range from 10,000 to 20 million. The term "non-emulsifying" defines a siloxane from which polyoxyalkylene units are absent. Advantageously the elastomers are formed from a divinyl compound, particularly a polymer with at least two free vinyl groups, reacting with Si—H linkages of a polysiloxane backbone such as a molecularly spherical MQ resin. Elastomer compositions are commercially available from the General Electric Company under product designation General Electric Silicone 1229 with proposed CTFA name of Cyclomethicone and Vinyl Dimethicone/Methicone Cross Polymer, delivered as 20–35% elastomer in a cyclomethicone carrier. A related elastomer composition under the CTFA name of Crosslinked Stearyl Methyl Dimethyl Siloxane Copolymer is available as Gransil SR-CYC (25–35% elastomer in cyclomethicone) from Grant Industries, Inc., Elmwood Park, N.J.

Amounts of the elastomer may range from 0.1 to 30%, optimally from 1 to 25%, most preferably from 10 to 20% by weight of the composition.

Minor adjunct ingredients may also be included in cosmetic compositions of this invention. These ingredients may be selected from preservatives, fragrances, anti-foam agents, opacifiers, colorants and mixtures thereof, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

A series of in vivo ultraviolet radiation screening tests were conducted to evaluate sunscreening activity. The base formula is outlined under Table I.

TABLE I

Base Formula

| COMPONENT | WEIGHT % |
| --- | --- |
| Isosteayl Patmitate | 6.0 |
| $C_{12}$–$C_{15}$ Alkyl Octanoate | 3.0 |
| Stearic Acid | 3.0 |
| Glycerin | 2.0 |
| PEG-100 Stearate | 2.0 |
| Methylparaben | 1.5 |
| Glycerol Hydrostearate | 1.5 |
| Stearyl Alcohol | 1.5 |
| Triethanolamine 99 | 1.2 |
| Dimethicone | 1.0 |
| Sorbitan Stearate | 1.0 |
| Magnesium Aluminum Silicate | 0.6 |
| Hydroxyethycellulose | 0.5 |
| Sodium Stearoyl Lactylate | 0.5 |
| Cholesterol | 0.5 |
| Xanthan Gum | 0.2 |
| Propylparaben | .10 |
| Disodium EDTA | 0.05 |
| Butylated Hydroxytoluene | .05 |
| Water | Balance |

The base formula outlined under Table I was then combined with dimethyl isosorbide, ferulic acid and/or a combination of these in Formulas A–C as follows:

Formula A=Base+10% Dimethyl isosorbide (Arlasolve DMI)

Formula B=Base+0.5% Ferulic acid

Formula C=Base+0.5% Ferulic acid+10% Dimethyl isosorbide.

Evaluations were conducted with a Rapid In-Vivo Screening test. Approximately 20 subjects participated. The test involved the radiation of a selected area covered with test product on an individual's skin for approximately two minutes. Observation of the exposed area was then performed at 72 hours, 120 hours and 160 hours. The following scale was employed.

0=No Tanning

1=Slight Tanning

2=Moderate Tanning

3=Strong Tanning

4=Darkest

Unlike SPF rating sunscreen tests which measure a composition's UV shield, the present evaluation reflects antioxidant activity which interferes with the skin tanning response. In essence this test measures a material's biological tanning preventative activity. Of course, the present invention and its materials should not be considered limited by the aforementioned mechanistic theory; other mechanistic pathways may be operative.

TABLE II

Sunscreen Results

| Test Product | Tanning 72 hrs. after UV Exposure | Tanning 120 hrs. after UV Exposure | Tanning 168 hrs. after UV Exposure |
|---|---|---|---|
| No Treatment | 1.13 | 1.54 | 1.41 |
| Formula A | 1.00 | 1.46 | 1.29 |
| Formula B | 0.86 | 1.14 | 1.04 |
| Formula C | 0.64 | 0.82 | 0.68 |

Results of the study are reported under Table II. The listed values were statistically significant at the 95% confidence level. From Table II it is seen that the least tanning (i.e. most effective sunscreen activity) is shown by Formula C. The decreased tanning is more than additive over values for Formula A and Formula B separately applied to the skin.

An additional benefit was found with respect to reduced skin irritation. Erythema generally reaches maximum at 72 hours. Formula C imparted substantially less erythema to the UV exposed skin than treatments with either Formula A or B. See Table III (scale same as above for tanning).

TABLE III

| Test Product | Erythema 72 hrs. after UV Exposure |
|---|---|
| No Treatment | 1.09 |
| Formula A | 0.96 |
| Formula B | 0.93 |
| Formula C | 0.43 |

EXAMPLES 2–5

A series of further examples accordingly to the present invention are outlined under Table II. These formulations provide good storage stability and will have excellent anti-tanning performance.

TABLE II

| COMPONENT | Example No. (Weight %) | | | |
|---|---|---|---|---|
| | 2 | 3 | 4 | 5 |
| Cyclomethicone | 42.0 | 41.6 | 40.0 | 42.0 |
| Gransil SR CYL | 18.0 | 17.9 | 17.3 | 18.0 |
| Propylene Glycol | 16.8 | 14.8 | 17.5 | 15.0 |
| Polyethylene Glycol 200 | 11.0 | 13.7 | 13.5 | 13.5 |
| Ferulic Acid | 2.0 | 1.0 | 3.5 | 0.1 |
| Dimethyl Isosorbide | 2.0 | 2.0 | 2.0 | 2.0 |
| Cetyl Dimethicone Copolyol | 0.8 | 0.8 | 0.8 | 0.8 |
| Water | balance | balance | balance | balance |

EXAMPLES 6–12

These series of Examples illustrate the scope of the present invention, Various concentrations and different glycol carriers are illustrated.

TABLE III

| COMPONENT | Example No. (Weight %) | | | | | | |
|---|---|---|---|---|---|---|---|
| | 6 | 7 | 8 | 9 | 10 | 11 | 12 |
| Cyclomethicone | 36.0 | 36.0 | 36.0 | 40.0 | 40.0 | 45.0 | 32.0 |
| Gransil SR CYL | 24.0 | 24.0 | 24.0 | 20.0 | 20.0 | 15.0 | 27.0 |
| Butylene Glycol | 17.5 | — | 17.5 | — | — | — | 29.0 |
| Glycerin | — | 17.5 | — | — | — | — | — |
| Polyethylene Glycol 200 | 10.0 | — | — | 17.5 | 12.0 | 10.0 | 10.0 |
| Polyethylene Glycol 800 | — | 10.0 | 10.0 | 10.0 | 12.0 | 10.0 | — |
| Dimethyl Isosorbide | 2.0 | 2.0 | 2.0 | 4.0 | 8.0 | 10.0 | 1.0 |
| Ferulic Acid | 1.0 | 1.0 | — | 4.0 | — | 8.0 | 0.5 |
| Octyl Ferulate | — | — | 1.0 | — | — | — | — |
| Ethyl Ferulate | — | — | — | — | 4.0 | — | — |
| Cetyl Dimethicone Copolyol | 0.8 | 0.8 | 0.8 | 0.8 | 0.8 | — | — |
| Water | bal. | bal. | bal. | bal. | bal. | bal. | bal. |

The foregoing description and Examples illustrate selected embodiments of the present invention and in light thereof variations and modifications will be suggested to one skilled in the art, all of which are within the spirit and purview of this invention.

What is claimed is:

1. A cosmetic composition comprising:

(i) from 0.01 to 5% by weight of ferulic acid;

(ii) from 0.1 to 20% by weight of dimethyl isosorbide; and (iii) a pharmaceutically acceptable carrier.

2. The composition according to claim 1 wherein the carrier comprises a polyol in an amount from 1 to 50% by weight of the composition.

3. The composition according to claim 2 wherein the polyol is selected from the group consisting of propylene glycol, dipropylene glycol, polypropylene glycol, polyethylene glycol, sorbitol, hydroxypropyl sorbitol, hexylene glycol, 1,3-butylene glycol, 1,2,6-hexanetriol, glycerin, ethoxylated glycerin, propoxylated glycerin and mixtures thereof.

4. The composition according to claim 2 wherein the polyol is a mixture of polyethylene glycol and propylene glycol in a weight ratio of 5:1 to 1:10.

5. The composition according to claim 1 wherein the amount of ferulic acid is present from 0.1 to 3% by weight of the composition.

6. The composition according to claim 1 further comprising from 0.1 to 30% of a crosslinked non-emulsifying siloxane elastomer.

7. The composition according to claim 1 wherein the crosslinked non-emulsifying siloxane elastomer is formed from a divinyl monomer reacting with Si—H linkages of a polysiloxane.

8. The composition according to claim 1 further comprising from 10 to 80% of a volatile siloxane.

9. The composition according to claim 1 wherein the dimethyl isosorbide is present in an amount from 0.5 to 10% by weight.

* * * * *